United States Patent
Gozani et al.

(10) Patent No.: US 7,493,157 B2
(45) Date of Patent: Feb. 17, 2009

(54) DEVICES AND METHODS FOR THE NON-INVASIVE DETECTION OF SPONTANEOUS MYOELECTRICAL ACTIVITY

(76) Inventors: Shai N. Gozani, 187 Mason Ter., Brookline, MA (US) 02446; Steven P. Keller, 63 Abrams Ct., Apt. #8D, Stanford, CA (US) 94305

( * ) Notice: Subject to any disclaimer, the term of this patent is extended or adjusted under 35 U.S.C. 154(b) by 1306 days.

(21) Appl. No.: 10/279,662

(22) Filed: Oct. 24, 2002

(65) Prior Publication Data

US 2004/0225211 A1 Nov. 11, 2004

Related U.S. Application Data

(60) Provisional application No. 60/335,061, filed on Oct. 24, 2001.

(51) Int. Cl.
   *A61B 5/04* (2006.01)
(52) U.S. Cl. .................................... 600/546
(58) Field of Classification Search ................. 600/546
   See application file for complete search history.

(56) References Cited

U.S. PATENT DOCUMENTS

| | | | |
|---|---|---|---|
| 4,170,225 A | * | 10/1979 | Criglar et al. ............... 600/546 |
| 4,817,606 A | | 4/1989 | Lekholm |
| 5,505,208 A | * | 4/1996 | Toomim et al. ............. 600/546 |
| 5,551,445 A | * | 9/1996 | Nashner ...................... 600/595 |
| 5,573,011 A | * | 11/1996 | Felsing ........................ 600/595 |
| 5,857,980 A | | 1/1999 | Wilson |
| 6,010,468 A | * | 1/2000 | Grove et al. .................. 601/23 |
| 6,014,588 A | | 1/2000 | Fitz |
| 6,351,665 B1 | | 2/2002 | Koch |

* cited by examiner

*Primary Examiner*—Max Hindenburg
*Assistant Examiner*—H. Q. Nguyen
(74) *Attorney, Agent, or Firm*—Pandiscio & Pandiscio

(57) ABSTRACT

A method of detecting neuromuscular pathology in an individual is disclosed comprising the steps of placing a detector on the skin surface of the individual substantially adjacent to a skeletal muscle; obtaining signals from the detector; processing the signals; and determining neuromuscular status in response to the signals. A system for detecting neuromuscular disease in an individual is disclosed, the system comprising at least one means for recording a first signal from a skeletal muscle; a filter in communication with the recording means to generate a second signal consisting substantially of spontaneous myoelectrical activity; and a processor in communication with the filter, wherein the first signal from the skeletal muscle is filtered so as to generate spontaneous myoelectrical signals, and further wherein the processor calculates the power spectral density of the filtered signals and determines the neuromuscular status in response to the power spectral density of the filtered signals.

28 Claims, 14 Drawing Sheets

TABLE II
MEAN dB DIFFERENCE BETWEEN DENERVATED AND
NORMAL MUSCLE SIGNALS FROM 2500 HZ TO 4000 HZ

| Animal | DB Difference |
|--------|---------------|
| #1     | 0.015 dB      |
| #2     | 1.16 dB       |
| #3     | -0.026 dB     |

TABLE IV
MEAN dB DIFFERENCES BETWEEN NORMAL AND DENERVATED MUSCLE
SIGNALS AT VARIOUS FREQUENCY BANDS

| Animal | 100-300 Hz | 100-500 Hz | 800-1000 Hz |
|--------|-----------|-----------|-------------|
| #1     | 3.427     | 2.672     | 0.609       |
| #2     | 1.898     | 1.727     | 0.477       |
| #3     | 3.023     | 2.772     | 0.461       |

FIG. 13

Determine Power Level of Motor Activity — 810

Calculate PSD of filtered data for healthy and symptomatic muscles of interest — 1302

Calculate energy in signal bandwidth — 1304

Calculate energy in noise bandwidth — 1306

Calculate SNR for healthy and symptomatic muscles — 1308

DEVICES AND METHODS FOR THE NON-INVASIVE DETECTION OF SPONTANEOUS MYOELECTRICAL ACTIVITY

REFERENCE TO PENDING PRIOR PATENT APPLICATION

This patent application claims benefit of pending prior U.S. Provisional Patent Application Serial No. 60/335,061, filed Oct. 24, 2001 by Shai N. Gozani et al. for DEVICES AND METHODS FOR THE NON-INVASIVE DETECTION OF SPONTANEOUS MYOELECTRICAL ACTIVITY, which patent application is hereby incorporated herein by reference.

FIELD OF THE INVENTION

This invention relates to devices and methods for the non-invasive detection of spontaneous bioelectrical activity generated from skeletal muscle fiber or nervous tissue, and more particularly to the non-invasive detection of neuromuscular pathology resulting from muscle full or partial denervation.

BACKGROUND OF THE INVENTION

Fibrillation potentials are a form of spontaneous muscle activity arising from single muscle fibers. The presence of these potentials are consistent with muscle denervation. The detection of fibrillation potentials can indicate underlying neuromuscular pathologies, including cervical or lumbosacral radiculopathies, entrapment neuropathies, demyelinating, polyneuropathies, or genetic or acquired myopathies.

Radiculopathies are diseases of the spinal nerve roots as they exit the spinal cord. They are most commonly caused by compressive processes such as intervertebral disc protrusion and degenerative osteoarthritis. Compressive radiculopathies of the lumbosacral and cervical regions are frequent and dangerous causes of lower back and neck pain, respectively. Back pain resulting from a radiculopathy is serious and may require surgery.

The detection of spontaneous muscle electrical activity is typically performed using needle electromyography (NEMG). This technique comprises inserting a needle electrode into the muscle of interest and passively observing the spontaneous bioelectrical activity. The bipolar concentric needle, the most commonly used needle electrode in clinical practice, records a differential signal at the tip of the needle referenced to either another needle electrode placed subcutaneously or a surface electrode. Insertion of the needle electrode results in a burst of electrical activity as the tip of the needle damages muscle fiber membranes, which quickly subsides once the needle ceases to move. In a fully relaxed, healthy muscle, there is no muscle generated bioelectrical activity.

The use of needle electromyography (NEMG) has several disadvantages. A typical electromyographic examination requires multiple needle insertions. The needle must be repositioned multiple times at each insertion point to ensure adequate spatial sampling of the muscle of interest. This procedure is consequently an invasive and painful method with a nominal risk of infection or bleeding. Furthermore, the procedure is expensive and cannot often be obtained for most patients unless the symptoms are severe and surgery is an immediate possibility. The invasive nature, cost and required expertise of NEMG limits its use to the late confirmation of suspected pathology and makes longitudinal patient monitoring impractical.

Conventional surface electromyography (SEMG) techniques are currently limited in their clinical use due to their lack of spatial resolution. SEMG techniques, in which the spectral characteristics of the signal are analyzed, are used to examine muscle fatigue as an indicator of neuromuscular pathology.

SUMMARY OF THE INVENTION

The present invention is directed to devices and methods for the non-invasive detection of spontaneous myoelectrical activity, an indicator of neuromuscular pathology or disease, generated from skeletal muscle. According to the invention, one method includes the steps of placing a detector on the surface of the skin of an individual that is substantially adjacent or proximal to a skeletal muscle referred to as the target muscle, recording signals potentially comprising spontaneous myoelectrical activity received from the detector, and processing those signals for the purpose of determining the neuromuscular status of the skeletal muscle with respect to the presence of neuromuscular disease.

Myoelectrical activity may comprise bioelectric or biopotential signals. The processing step can include removing external electrical interference signals, removing neurogenic muscle signals or removing signals generated from muscles other than those generated from the target muscle. Neurogenic muscle signals can include voluntary or involuntary neurogenic muscle signals. Involuntary neurogenic muscle signals can include those generated from normal muscle activation or caused by a pathology.

The processing step can also include determining one or more spectral characteristics, such as determining the power spectral density of the detected bioelectrical or biopotential signals. Optionally, the power spectral density of the detected signals can be displayed. In some embodiments, the power spectral density is determined within one or more particular ranges of signal frequencies. In one embodiment, the signal frequency range is between 100-500 Hz. In another embodiment, this range is between 300-500 Hz.

In some embodiments, the processing step includes comparing one or more characteristics of the detected signals against at least one reference value for each of the one or more characteristics associated with the detected signals. Optionally, characteristics of the detected signals can be derived from the power spectral density of the detected signals. In another aspect, characteristics of the detected signals can be derived from spectral characteristics other than the power spectral density of the detected signals. In another aspect, differences between the characteristics of the detected signals and the reference values are used as indicators of the neuromuscular status of the target muscle, including the presence and degree of neuromuscular pathology or disease. Relative values quantifying the degree of neuromuscular disease can be computed from differences in characteristics and displayed. The status of neuromuscular disease is selected from the group of diseases consisting of radiculopathies, demyelinating neuropathies, intravertebral disc disease, and carpal tunnel syndrome.

In an alternative embodiment, the processing step can include comparing one or more characteristics of signals detected at a first point in time to signals detected at a second point in time to monitor the progression of the degree or extent of neuromuscular disease. In another embodiment, the processing step comprises comparing at least one characteristic of the processed signal of the individual with a reference value.

In another embodiment, a method for detecting a neuromuscular pathology or for detecting a disease of nerve innervating a skeletal muscle includes the steps of measuring a first signal from a detector positioned substantially adjacent or proximal to the skeletal muscle, removing noise to generate a second signal including substantially spontaneous myoelectrical activity, processing the second signal and determining the neuromuscular status of the skeletal muscle from the processed second signal. In one embodiment, the noise includes voluntary neurogenic myoelectrical activity. In one embodiment, the determination of the neuromuscular status includes the step of determining the power spectral density of the second signal, obtaining reference values, and comparing the power spectral density of the second signal and the reference values to indicate the presence and extent of neuromuscular pathology. Optionally, the power spectral density of the second signal is displayed and relative values quantifying the degree of neuromuscular pathology can be determined and displayed.

The invention provides a system for detecting neuromuscular pathology in a skeletal muscle or detecting disease of a nerve innervating the skeletal muscle of an individual. This system includes a means for detecting and recording a first signal from the skeletal muscle, a filter in communication with the recording means to generate a second signal of substantially spontaneous myoelectrical activity, and a processor in communication with the filter. Signals from the skeletal muscle are filtered to generate spontaneous myoelectrical signals and the processor calculates the power spectral density of the filtered signals and determines the neuromuscular status from the power spectral density of the filtered signals. The invention also provides a system for detecting neuromuscular pathology in a skeletal muscle or a nerve innervating the skeletal muscle of an individual. The system comprises at least one surface recording electrode for measuring a signal from the skeletal muscle, a first filter for filtering spontaneous myoelectrical signals to generate a first set of filtered signals, a second filter for removing noise from the first set of filtered signals to generate a second set of filtered signals, and a processor for calculating the power spectral density of the second set of filtered signals and for determining the presence of pathology in skeletal muscle or the presence of nerve innervating skeletal muscle of the individual in response to the power spectral density of the set of second filtered signals. In one embodiment, noise resides in a first frequency range below about 0.1 Hz and and in a second frequency range above about 10,000 Hz.

BRIEF DESCRIPTION OF THE DRAWINGS

The invention is pointed out with particularity in the appended claims. The advantages of the invention described above, as well as further advantages of the invention, may be better understood by reference to the following detailed description taken in conjunction with the accompanying drawings, in which:

FIG. 4 lists the mean relative difference, calculated in dB, between the signal strength of denervated and normal muscle over the muscle activity frequency band referenced to a noise frequency band of 2500-4000 Hz.

FIG. 5 (Table IV) lists the mean relative difference, calculated in dB, between the signal strength of denervated and normal muscle in various frequency ranges.

FIG. 13 is a flow diagram illustrating an embodiment of the steps performed to determine the power level of motor activity.

DETAILED DESCRIPTION OF THE INVENTION

The devices and methods of the invention provide for the non-invasive detection of spontaneous myoelectrical activity generated from skeletal muscle. The presence of spontaneous myoelectrical activity within muscle is an important diagnostic indicator of neurological or neuromuscular pathology. As the term is used throughout, neuromuscular pathology means the presence of pathology in nerve roots, nerves or muscles. Accordingly, the invention is particularly useful for the non-invasive detection and diagnosis of neuromuscular pathology, such as caused by cervical and lumbrosacral radiculopathy, demyelinating polyneuropathies, intravertebral disc disease, and entrapment neuropathies such as carpal tunnel syndrome. Some causes of neuromuscular pathology can lead to muscle denervation and increased spontaneous myoelectric activity within the affected muscle tissue resulting from muscle fiber fibrillation potentials or positive sharp waves (PSW). Physicians can use the presence and level of spontaneous myoelectric activity in a patient to diagnose and stage neuropathology as well as to develop and monitor therapeutic interventions.

A non-invasive method of detecting spontaneous muscle activity has the advantage of increasing patient acceptance by reducing patient anxiety associated with the pain and discomfort of invasive methods. Increased patient acceptance can allow physicians to more frequently use this type of diagnostic to monitor patient responses to treatment and to enable an improvement in clinical outcomes. The potential for the standardization of a non-invasive method could enable primary-care physicians to use this type of diagnostic test to improve early diagnosis and to screen high-risk patients.

Figure 1:
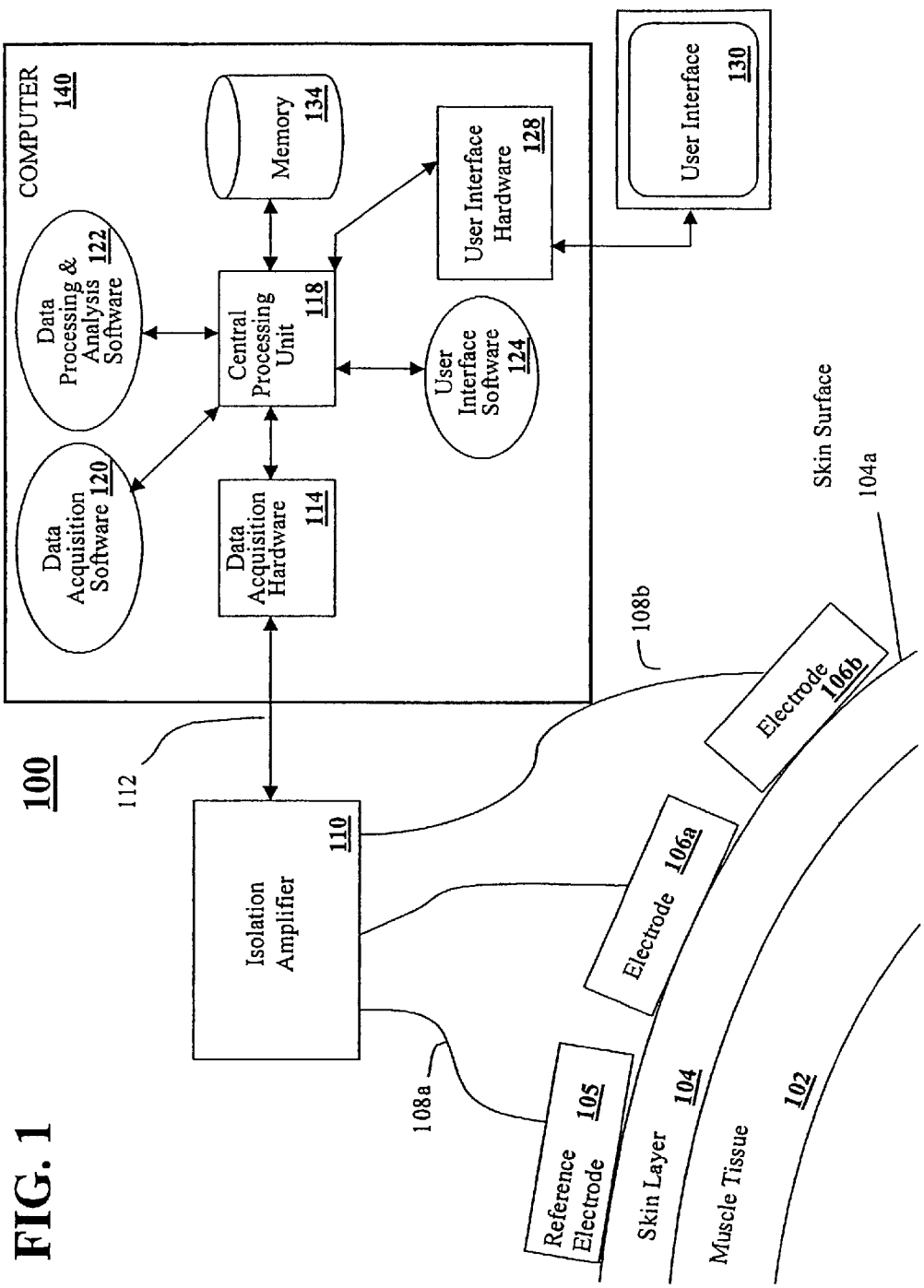
FIG. 1 is a conceptual block diagram illustrating an embodiment of a system constructed according to the invention.

FIG. 1 is a conceptual block diagram illustrating the preferred embodiment of a system 100. In this embodiment, two electrodes 106a, 106b, and a reference electrode 105 are detectors configured for placement onto the outer surface of the skin 104a adjacent to or within proximity to a skeletal muscle tissue 102, which is selected to be monitored for spontaneous myoelectrical activity. Reference electrode 105 acts as a point of biopotential reference relative to the biopotential measured by electrodes 106a and 106b. Measurements of signal activity by the two electrodes 106a and 106b are relative to the reference electrode 105. Electrodes 106a and 106b detect and communicate signals representing the presence of myoelectrical activity within the proximity of skeletal muscle tissue 102 to an isolation amplifier 110 via one or more electronic connections 108a, 108b. Isolation amplifier 110 amplifies, filters and re-communicates the signals received from the electrodes 106a and 106b to data acquisition hardware 114 as via a separate electrical connection 112. In one embodiment, a World Precision Instruments (ISO-DAM) isolation amplifier is utilized to low pass filter signals less than 10K Hz, and high pass filter signals greater than of 0.1 Hz, and amplify the signals by a factor of 1000.

In this embodiment, data acquisition hardware 114 resides as a component of the computer and operates under the control of the data acquisition software 120. Data acquisition software 120 controls the operation of data acquisition hardware 114 by executing instructions via central processing unit 118 of computer 140. Data acquisition hardware 114, as directed by data acquisition software 120, stores information representing the signal activity received from isolation amplifier 110 into memory 134 of computer 140. In one embodiment, a National Instruments Data Acquisition Card is used as data acquisition hardware 114 while the National Instruments CVI/Lab Windows data acquisition program is used as data acquisition software 120. The software 120 provides an amplification gain setting of 10, which in combination with the amplification gain setting of isolation amplifier 110 results in a total signal gain of 10,000.

In a particular embodiment, data acquisition hardware 114 stores myoelectrical signal data into a memory 134. Myoelectrical activity is typically detected continuously within a fixed period of time, referred to as a recording session. The length of the recording session is preferably between 1 second and 300 seconds. In one embodiment, the length of a recording session is 120 seconds in length. However, durations shorter than 1 second or longer than 300 seconds, and of sufficient length to capture particular spectral characteristics have been considered and should be viewed as within the scope of the present invention. Myoelectrical activity detected within one recording session is typically stored separately from the myoelectrical activity detected within other recording sessions. Multiple recordings of myoelectrical signal activity can be recorded from the same set of electrode positions at different times or from different sets of electrode positions at the same or different times.

Data processing and analysis software 122 further processes or transforms the data in preparation for analysis. The recorded activity is processed via a plurality of transformations implemented as software algorithms executing within data transformation and analysis software 122. These transformations include further amplification, notch filtering and the alteration of background noise to offset the differences in background noise between separate recordings of the myoelectrical signals. In the one embodiment, a second order Chebyshev notch filter is used to reduce the level of 60 Hz noise and associated harmonics via a MATLAB Cheby2 software routine (Mathworks, Inc., Natick, Mass.)) with a 20 decibel reduction in signal energy. The harmonics of 60 Hz noise are not filtered.

Next, data processing and analysis software 122 performs the identification and removal of neurogenic myoelectric signal activity from the myoelectric signal activity data. Neurogenic muscular activity is nerve initiated muscle activity. Neurogenic myoelectric activity includes voluntary and involuntary myoelectric activity. Voluntary myoelectric activity is normal myoelectric activity generated when a patient willfully activates a muscle, such as, for example, when a patient willfully flexes a bicep muscle. Involuntary myoelectric activity is myoelectric activity generated by a muscle caused from means other than willful muscle activation. For example, a bicep muscle in a relaxed state may generate myoelectrical activity without any willful activation by the patient. Alternatively, a nerve pathology such as Parkinson's disease may cause the generation of myoelectrical activity without any willful muscle activation by the patient.

Nerve initiated muscle activity typically involves the simultaneous activation of many muscle fibers. Spontaneous muscle activity typically involves the activation of individual muscle fibers at times that are independent of each other. After transforming the myoelectrical signal activity data via removal of neurogenic myoelectrical activity, noise and possible spontaneous myoelectrical activity may remain within the transformed myoelectrical signal activity data.

Next, the data processing and analysis software 122 performs spectral analysis of the transformed signal activity. Spectral analysis can identify the presence of any spontaneous myoelectrical activity remaining within the transformed signal activity. In one embodiment, spectral analysis includes the determination of the power spectral density of the transformed signal activity within particular ranges of signal frequency. Differences between the power spectral density of the transformed signal activity between particular ranges of signal frequency can be indicative of spontaneous myoelectrical activity. The identification of spontaneous myoelectrical activity supports the determination of the presence of neuromuscular pathology within the selected muscle tissue.

Experimental use of an embodiment of the invention reveals that the power spectral density of the myoelectric activity of denervated muscle tissue is measurably higher than of non-denervated muscle tissue of laboratory rats within the 100-500 Hz range of signal frequency. The mean power ratio between denervated and non-denervated muscle tissue was 2.78 dB (decibels) in the 100-300 Hz frequency band and 2.39 dB in the 100-500 Hz frequency band. A predictive computer model of the relative myoelectric signal generation of denervated and non-denervated muscle tissue for the parameters of the above experiment has yielded similar results.

In one embodiment, the software 122 determines the power spectral density using the Welsh method with an Fast Fourier Transform (FFT) length of 8192 and a Hamming window length of 8192. There is no overlap of sample windows over the 100-500 Hz range of frequency. To reduce the contribution of harmonics to the calculation, 5 Hz windows of data, centered about each 60 Hz harmonic present in the 100-500 Hz frequency range, are not included in the power spectral density calculation.

Software 122 determines the presence of neuromuscular pathology in the selected muscle tissue based upon a comparison of the power spectral density of the monitored muscle tissue as compared to that of the reference data. The reference data or reference muscle data may be data representing signals that are recorded from normal muscle tissue or alternately, the reference data may be recorded from muscle tissue with a known amount or percentage of denervation. Reference data can also be that produced from the output of the computer modeling of muscle fibers. Differences between the power spectral density of the monitored muscle tissue and the power spectral density of muscle tissue as represented by reference data can be indicative of the level of neuromuscular pathology.

Before the spectral analysis step, software 122 also implements a noise correction factor that is calculated by averaging the difference in signal energy in the high frequency band (2500-4000 Hz) between the recorded signal activity data for the selected muscle tissue and the signal activity of the reference muscle data. Where muscle tissue is selected from a test individual, reference data may be obtained from other muscle tissue of the test individual or from other individuals with similar physical attributes. As will be discussed, there are many alternative methods of obtaining reference data.

The results of data acquisition, processing, and analysis are communicated to a user via a user interface 130, which may comprise of a bitmap display screen, keyboard and screen pointer. In other embodiments, user interface 130 comprises a LCD screen and various switches. In yet another embodiment, the user interface 130 comprises of several light emitting diodes (LEDs) and switches. User interface software 124 outputs the results of the analysis of the data processing and analysis software 122 to the user.

Figure 2:
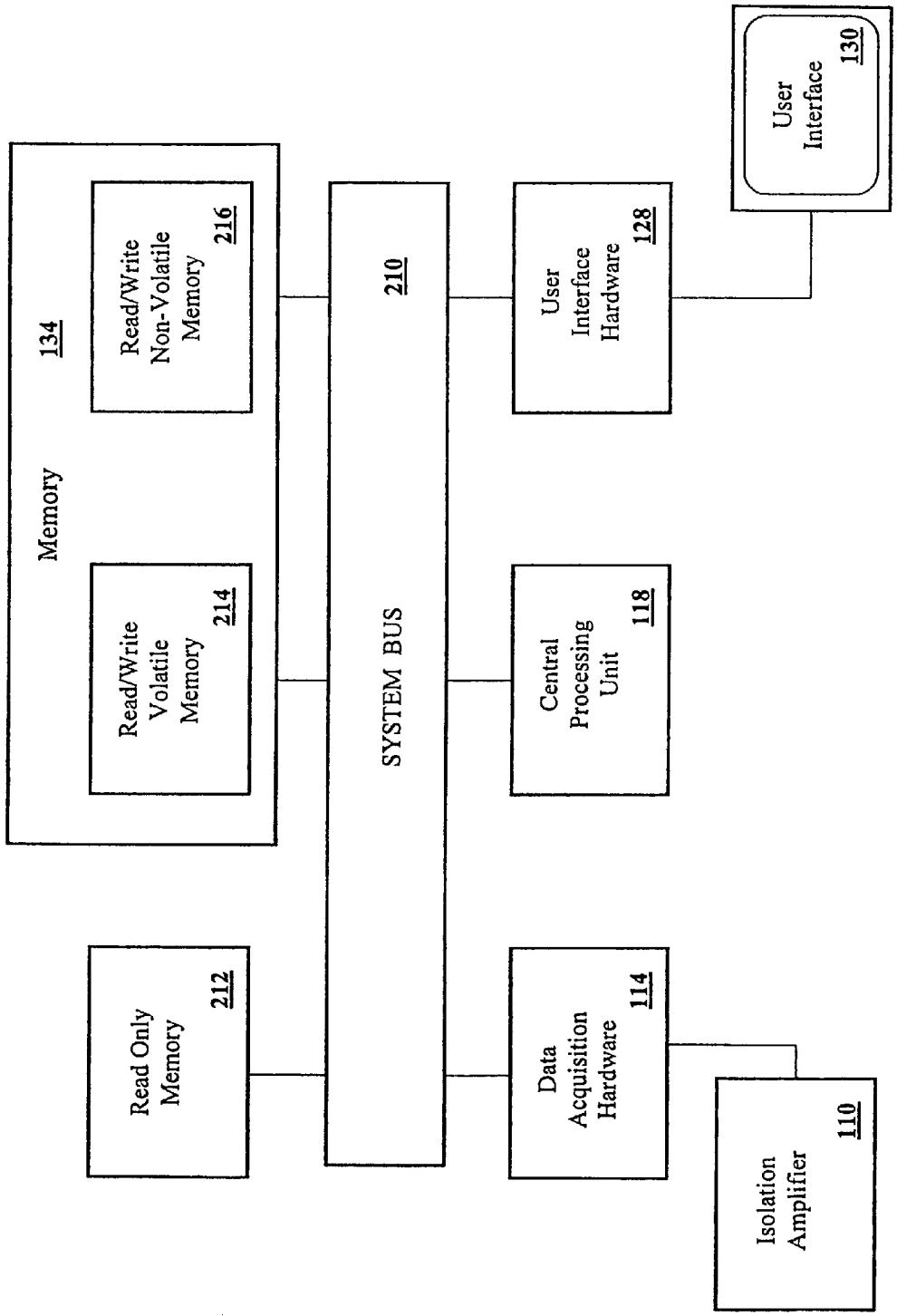
FIG. 2 is a block diagram illustrating the interconnection of hardware components residing within the computer of the embodiment of the system of FIG. 1.

FIG. 2 is a block diagram 200 illustrating the interconnection of hardware components residing as components of computer 140 of an embodiment of the system 100. A system bus 210 electronically connects a central processing unit 118, data acquisition hardware 114, read/write memory 134, and user interface hardware 128 to enable communication with each other. The read/write memory 134 includes volatile memory 214. This volatile memory 214 may include, for example, random access memory (RAM) and non-volatile mass storage memory including, without limitation, hard disks. Read/write memory 134 excludes read-only memory 212. Data acquisition hardware is connected to the isolation amplifier 110. User interface hardware 128 is connected to the user interface 130.

Figure 3:
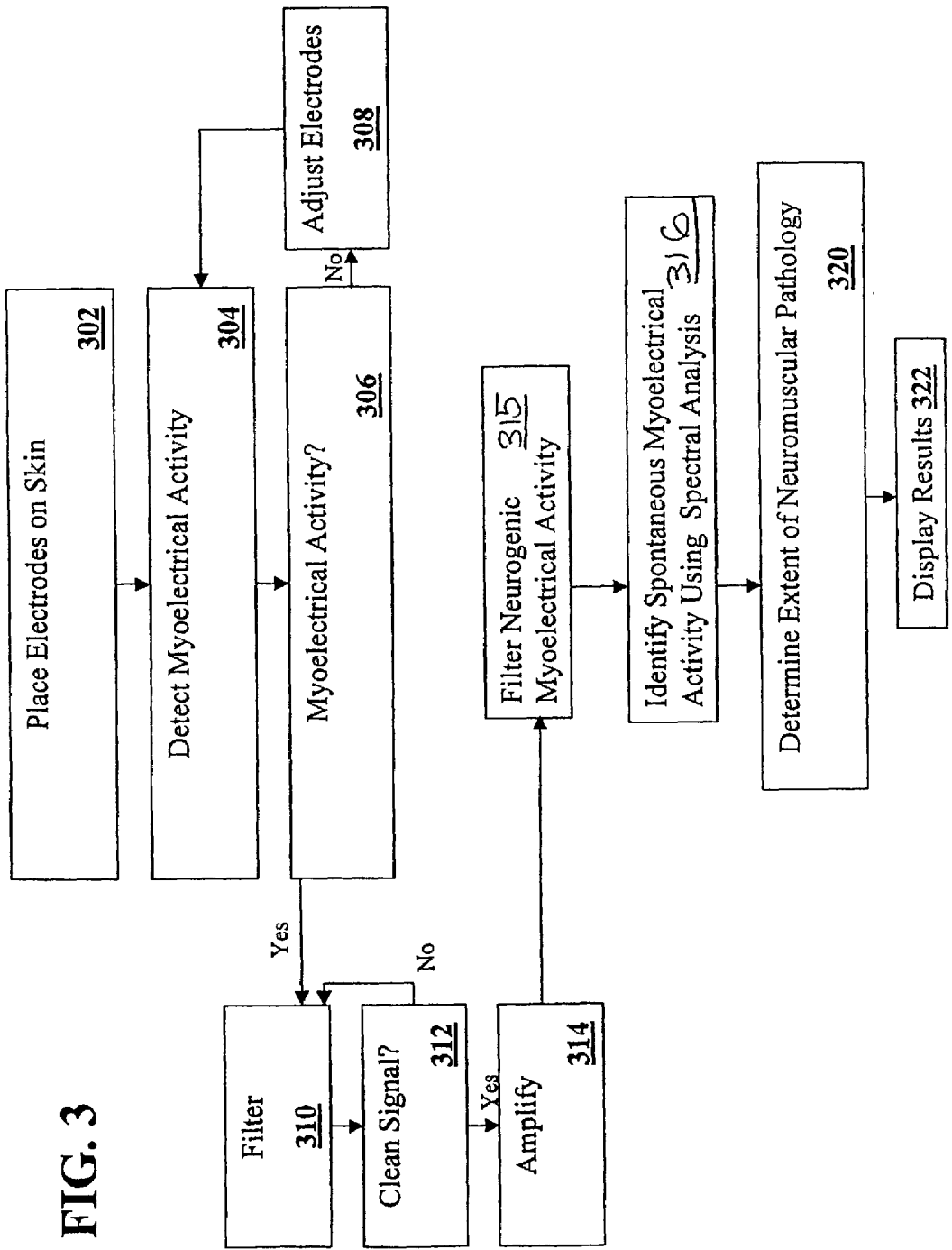
FIG. 3 is a flow diagram illustrating an embodiment of the steps for the non-invasive detection of spontaneous myoelectrical signal activity and the determination of neuromuscular pathology within muscle tissue according to the invention.

FIG. 3 is a conceptual flow diagram illustrating an embodiment of the method of non-invasive detection of spontaneous myoelectrical signal activity within selected muscle tissue using the invention. A first step 302 of this method is to place electrodes 106a, 106b and a reference electrode 105 on the surface of skin 104a that is adjacent to or in proximity of the selected muscle tissue 102. The reference electrode 105 is typically placed within 10 centimeters of either electrode 106a, 106b. A second step 304 is to detect and capture the presence of spontaneous surface myoelectric signal activity, also referred to as myoelectric potentials, using placed electrodes 106a, 106b. If a weak signal is detected (Step 306), the electrodes are readjusted to locate a stronger signal (Step 308) and step 304 is repeated.

A next step 310 is to filter and process the signal, via low and high pass filtering, amplification, notch filtering and noise reduction. If the signal is not clean, meaning that it is not noise free (Step 312), further filtering (step 310) is applied. A filtered signal is further amplified (step 314). Next (step 315), the signal activity processed in step 314 is analyzed and transformed to identify and remove any neurogenic myoelectric signal activity.

Following this step 315, the myoelectric signal activity, processed in step 316, is further analyzed using spectral analysis. In one embodiment, spectral analysis includes determining the power spectral density of the myoelectric signal activity within particular ranges of signal frequencies. In one embodiment, the determined power spectral density is compared against the comparable power spectral density of appropriate reference data. In step 320, the presence and the extent of neuromuscular pathology from denervation within the selected muscle tissue is determined, and the results of step 320 are displayed in step 322. The extent can be represented by a relative value quantifying the extent of neuromuscular pathology.

In one embodiment, the method places electrodes into a bipolar configuration that are 5 millimeters apart. Recordings are made at a sampling frequency of 25 kHz for two minutes. Optionally, the determination of the neuromuscular status can be made based upon parameters entered into the computer via the user interface. For example, the size and type of muscle associated with the target muscle and that of the reference data may be used to determine the extent of muscular pathology of the target muscle.

Where muscle tissue is selected from a test individual, reference data may be obtained from other muscle tissue of the test individual. In situations where the muscle tissue to be diagnosed has a symmetrical counterpart within a test individual, both the tissue to be diagnosed and its symmetrical counterpart muscle tissue as reference data can be measured and compared against each other to assess relative presence of any suspected neuromuscular pathology. Where only one member of this symmetrical pair of muscle tissue is suspected of having neuromuscular pathology, the difference in the power spectral density between these two different but symmetrical muscle tissues can represent the extent of the presence of neuromuscular pathology of the selected muscle tissue relative to the absence of neuromuscular pathology of the non-selected muscle tissue.

Alternatively, the power spectral density of the selected muscle tissue of the test individual can be measured periodically over time. Comparison of power spectral density measurements performed before any suspicion of neuromuscular pathology within the selected muscle tissue can be used as reference data representing the expected power spectral density for the absence of neuromuscular pathology within the selected muscle tissue.

Alternatively, the power spectral density of the classification of selected muscle tissue of the test individual can be characterized over classification of other individuals with similar physical traits. These other individuals are referred to as reference individuals. For example, there may be little variation in the measured power spectral density among particular finger muscles having the same extent of denervation. For muscle tissues where this is true, pre-existing measured power signal density data from other individuals within the same classification as the test individual can be used as reference data.

Alternatively, a predictive model of the power spectral density of particular muscle tissues for a test individual or a classification of test individuals can be used as reference data. This is suitable when the results of the predictive model have been shown to correlate well with measured power spectral density data.

Animal experiments using an embodiment of the invention have revealed that the power spectral density of the myoelectric activity of denervated muscle tissue is measurably higher than of non-denervated muscle tissue of laboratory rats within the 100-500 Hz range of signal frequency.

As an example of the potential of this method of the invention, three male albino rats, animals 1, 2 and 3, each weighing between 250-300 g, were used for experiments. General anesthesia was induced with isoflurane and maintained with a 1% (v/v) isoflurane/oxygen mixture flowing at a rate of 200 cc/min. The left sciatic nerve of each animal was exposed at the mid-thigh level and transected approximately 1 cm above the bifurcation into the tibial and peroneal nerves. A 5 mm segment of nerve was removed to prevent nerve regeneration. Following surgery, each animal was placed in a standard maintenance cage where they were watered and fed daily by hospital staff. Two weeks after surgery was performed, the animals were retrieved from hospital care and prepared for data acquisition.

Previous experiments have shown that spontaneous muscle activity develops in rats by at least 3 days following nerve transection. Since the experiments described herein were conducted 14 days after nerve transection, the presence of fibrillation potentials was expected.

Before taking recordings, the animals were placed under anesthesia using the same procedure used for the surgery. While under anesthesia, the area of skin overlying the gastrocnemius muscle on each side of each animal was shaved using a razor blade. Following hair removal, the skin was thoroughly cleaned with isopropyl alcohol. These procedures were performed to minimize electrode impedance. After waiting for the exposed skin area to dry thoroughly, Nicolet (Nicolet Instrument Corporation, Madison, Wis.) Silver/Silver Chloride gel electrodes were applied to each animal. Each electrode was placed using a template to ensure that the electrode size and spacing was consistent from animal to animal.

Measurements were taken using a World Precision Instruments ISO-DAM (World Precision Instruments, Sarasota, Fla.) isolation amplifier. The low-pass filter setting was 10 kHz, the high-pass filter setting was 0.1 Hz, and the gain setting was 1000. The data was then read into a computer utilizing a National Instruments Data Acquisition Card (National Instruments Corporation, Austin, Tex.) 110 that was controlled via a CVI/LabWindows (National Instruments Corporation, Austin, Tex.) data acquisition program 120. The software program gain was set at 10 resulting in a total system gain of 10,000.

The electrodes were placed in a bipolar configuration with the ground electrode being placed on the animal's tail. The electrodes were 20 mm in length and 8 mm in width. The electrodes were placed in parallel, 5 mm apart. Recordings were taken on each side of each animal at a sampling frequency of 25 kHz for two minutes. The normal and denervated sides of each animal were recorded serially and in alternating order from one animal to the next.

In addition to the bandpass filtering implemented with hardware, a 2nd order Chebyshev notch filter was used to reduce the level of 60 Hz noise in step 310. The notch filter was designed and implemented using the MATLAB Cheby2 routine with a 20 decibel (dB) reduction in signal energy. The harmonics of the 60 Hz noise were not filtered as they varied significantly between recordings. The power spectral density (PSD) of the surface recordings was calculated with the same method as for the simulated data-by using the Welch method with an FFT length of 8192, Hamming window of length 8192, and no overlap of sample windows in step 316. Differences in spectral energy between denervated and normal muscle signals were calculated by averaging the dB difference between the signals over a range of frequencies in step 318. In order to reduce the contribution of 60 Hz harmonics to the calculation of the dB difference, 5 Hz windows of data centered about each 60 Hz harmonic present in the frequency range of interest were not included in the calculation.

Differences in the level of background noise between recordings was offset by a noise correction factor. This factor was calculated by averaging the difference in signal energy in a high frequency band (2500-4000 Hz) between normal and denervated recordings for each animal. The power spectrum of the normal recording was adjusted by the resultant noise correction factor in order to produce convergence with the denervated recording in the high frequency band. This method assumes that no physiological signal is present at high frequencies and that any difference between signals represents a change in the level of background noise.

FIG. 4 (Table II) lists the mean relative difference, calculated in dB, between the signal strength of denervated and normal muscle in the 2500-4000 Hz frequency range. Signals in this frequency range are assumed to be background noise. Animals #1 and #3 exhibited similar levels of background noise, 0.015 dB and -0.026 dB, respectively, and consequently had noise correction factors close to unity. Animal #2 had an average increase of 1.16 dB in signal power at high frequencies (2.5-4 kHz) in the denervated side over the normal side. To offset this difference in the background noise level, the normal recording of Animal #2 was adjusted upward by the noise correction factor. This adjustment was the equivalent of a reduction of 1.16 dB in the power difference between the denervated and normal signals of Animal #2 over all frequencies.

The noise correction factor adjusts the value of the power difference, as expressed in decibels, between the denervated and normal muscle signal activity. It is a constant that is expressed in decibels. It is either added or subtracted from a decibel value representing the power difference between the two signals. Adding or subtracting logarithmic values has the effect of multiplying or dividing the actual signal power difference ratio by a constant equal to ten raised to the power equal to the logarithmic value.

After recovery from surgery, the animals appeared generally healthy. Signs of denervation were clearly evident on the side of the animal on which surgery was performed. The animal dragged the denervated leg behind it as it moved in the cage and was unable to place weight on the denervated limb. There was also wasting of the denervated gastrocnemius muscle which was estimated to be at least a third smaller than the non-denervated control side for each animal.

FIG. 5 (Table IV) lists the mean relative difference, calculated in dB, between the signal strength of denervated and normal muscle in various frequency ranges. Three frequency bands were considered; a 100-300 Hz band to serve as the primary measure of difference between the two sides, a 100-500 Hz band to provide a measure over a broader frequency range, and a 800-1000 Hz band to examine the energy difference at higher frequencies. The difference in the two lower frequency bands demonstrated increased power in the denervated muscle relative to the control muscle. By contrast, the power difference in the high frequency band was considerably smaller.

Figure 6A:
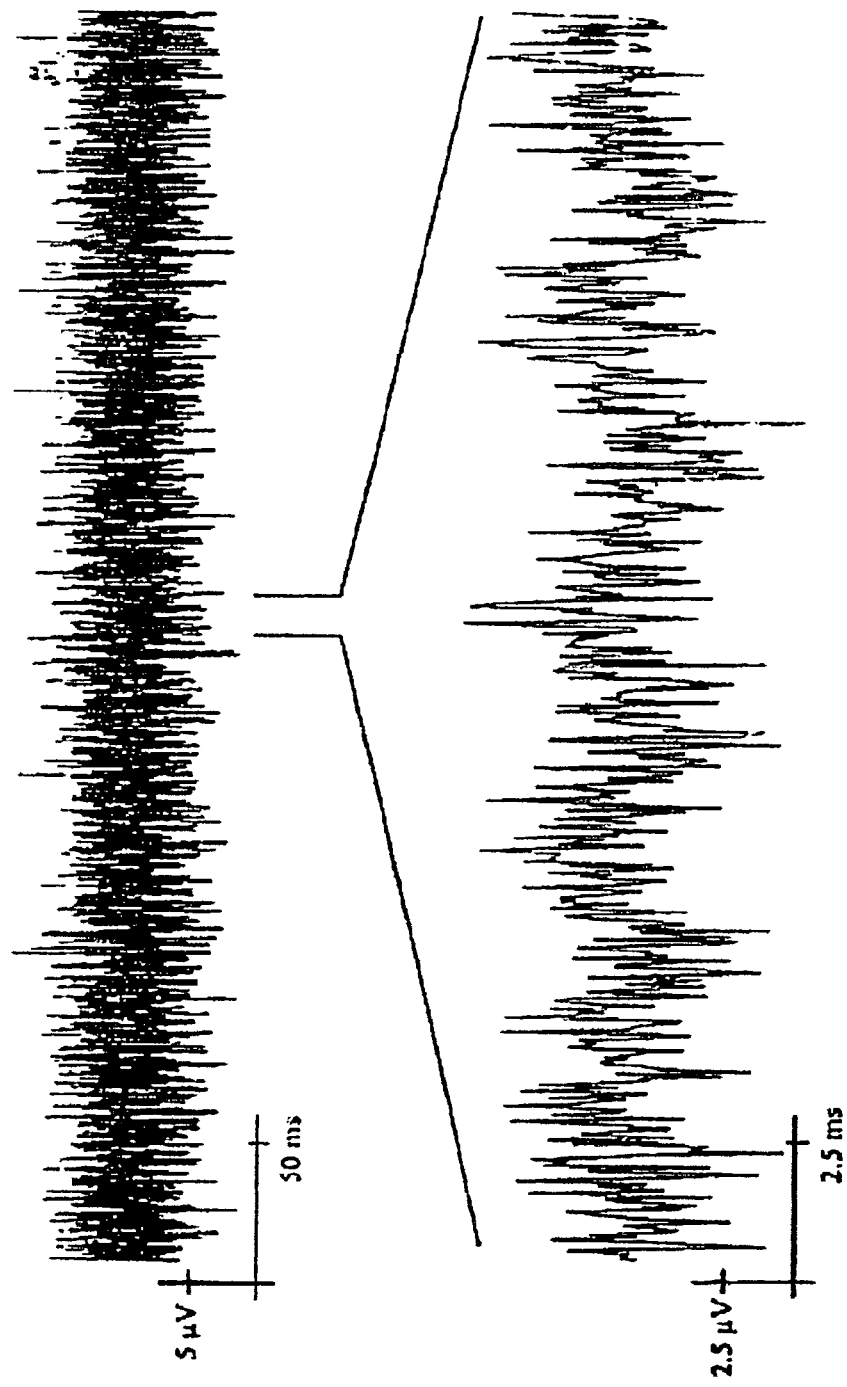
FIGS. 6A and 6B show typical time series signal data for the normal and denervated rat limb muscles.
Figure 6B:
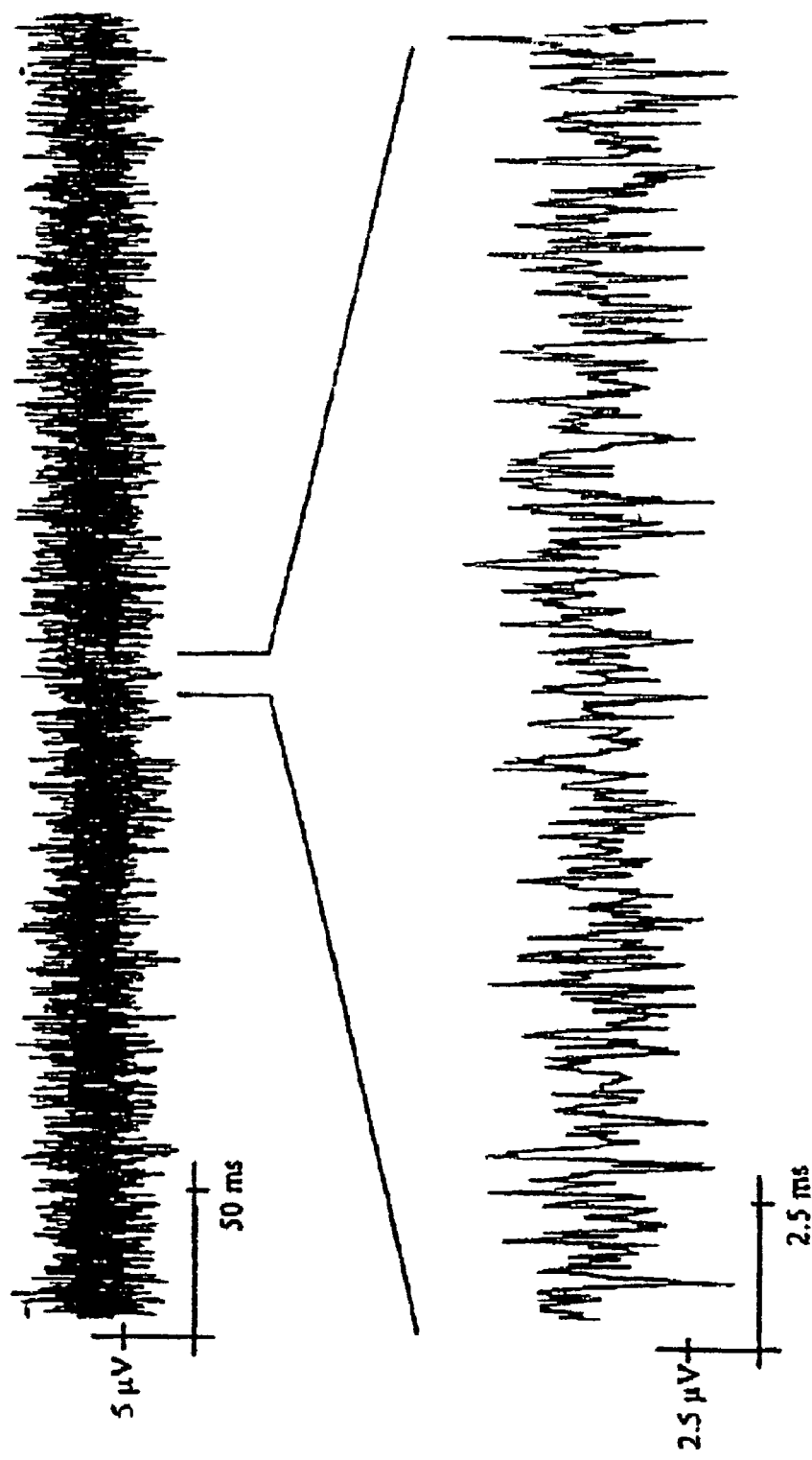

FIGS. 6A and 6B show typical time series signal data for the normal and denervated limb muscles. FIG. 6A represents data recorded from a control limb and FIG. 6B represents data recorded from the denervated limb of the same animal. There are no apparent time domain features that differentiate the two signals. In particular, there is no evidence of single muscle fiber action potentials in the denervated signal.

Figure 7:
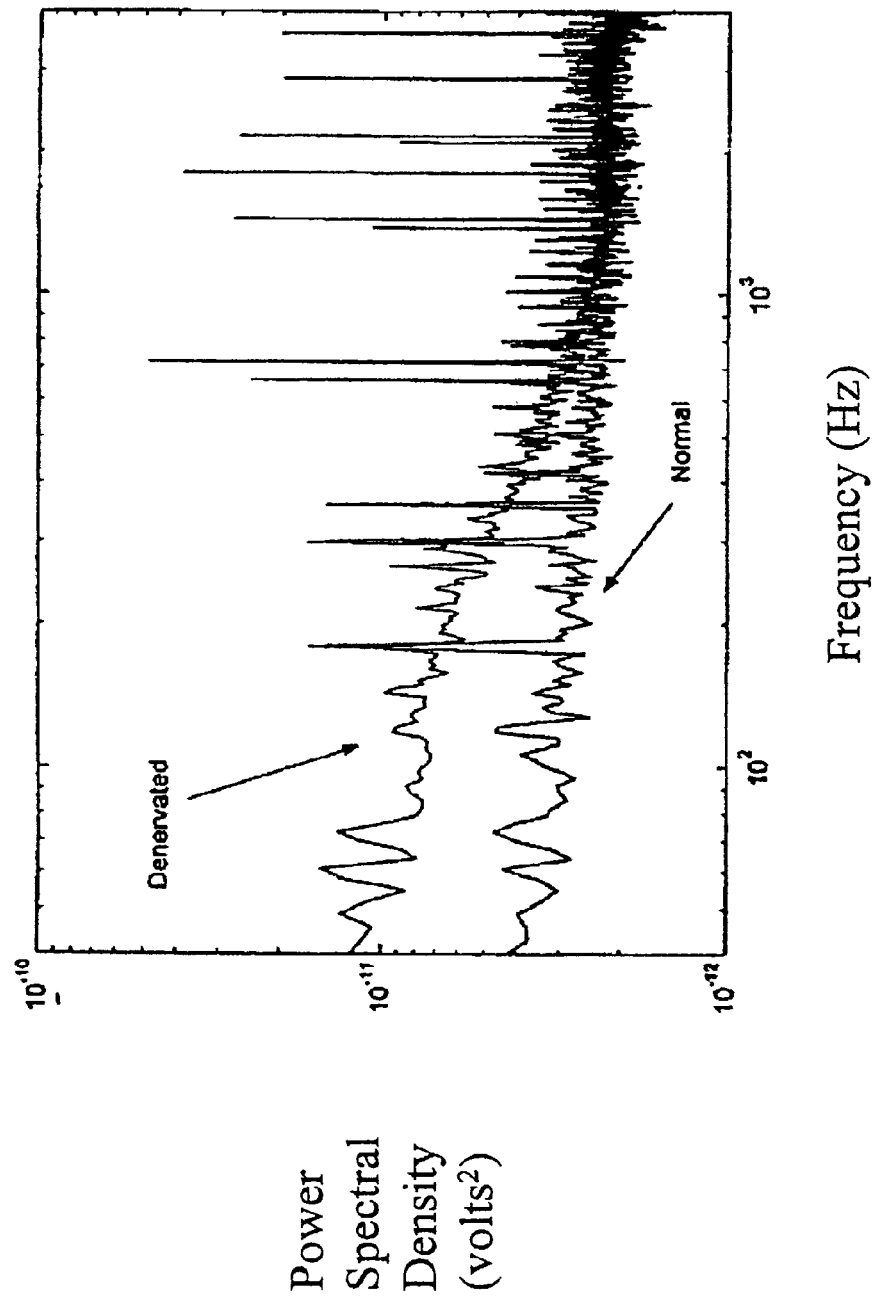
FIG. 7 shows the differences between the power spectral densities of signal data for the normal and denervated rat limb muscles.

By contrast, as illustrated in FIG. 7, the power spectral densities of the control and denervated limbs shown within the frequency domain demonstrate a clear difference. Although both spectral densities are strongly shaped by the filtering characteristics of the data acquisition hardware and post-processing, the denervated limb shows increased energy at frequencies below 1 kHz. Animal 2 and Animal 3 exhibited similar results. Very low frequency oscillations (<10 Hz) were observed in both denervated and normal muscle signals and were thought to be the result of electromagnetic contamination from nearby hospital equipment.

To summarize, animal experiments were conducted to obtain a preliminary indication of the viability of the hypothesis that spontaneous myoelectrical activity is detectable with surface electrodes. In contrast to NEMG, no coherent muscle activity or fibrillation potentials were discernible in the time domain data. The lack of time domain features emphasized the need for spectral analysis of surface recordings within the frequency domain. In each of the three animals tested, the power spectral density of the denervated limb had increased power over a band of frequencies similar to those predicted by the computer model. The mean power ratio between the denervated and control limb was 2.78 dB in the 100 to 300 Hz band and 2.39 dB in the 100 to 500 Hz band. This power difference was particularly impressive considering the presence of significant atrophy of the denervated gastrocnemius muscle.

A major determinant of whether spontaneous activity can be detected with surface electrodes is the level of background noise present in the recording system and at the electrode-skin interface. The utilization of low-noise components and input amplifiers with a high common mode rejection ratio acts to greatly improve the sensitivity of the system. Another contributor to the signal to noise ratio (SNR) is the signal itself. The degree of denervation, whether complete or partial, the size of the muscle affected, the proximity of the muscle to the skin surface, and the quality of the electrode-skin interface each affect the signal quality and the signal to noise ratio (SNR).

An additional factor that affects detection of fibrillation potentials is the presence of neurogenic muscle activity. Fibrillation potentials are a result of the firing of individual muscle fibers. Motor unit potentials are a result of the synchronous firing of multiple muscle fibers. As the basis is the same for both a motor unit potential and a fibrillation potential, the two different types of muscle activity contribute energy to the same frequencies so as to make spectral analysis difficult.

FIGS. 8-13 describe methods that identify and filter neurogenic myoelectrical signal activity, also referred to as neurogenic motor activity, from myoelectrical signal activity data.

Figure 8:
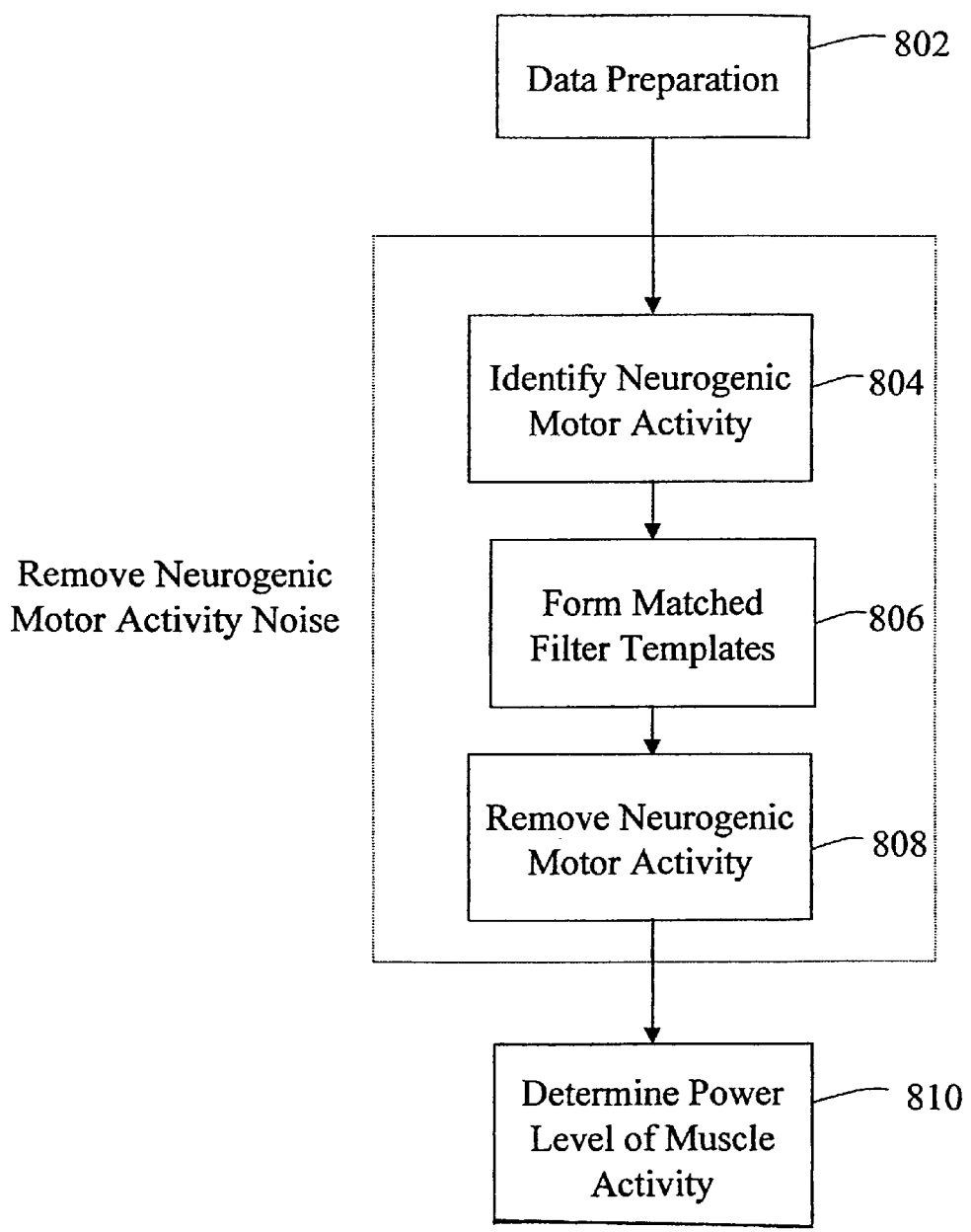
FIG. 8 is a flow diagram illustrating an embodiment of the steps performed by the spontaneous muscle activity signal processing algorithms.
Figure 9:
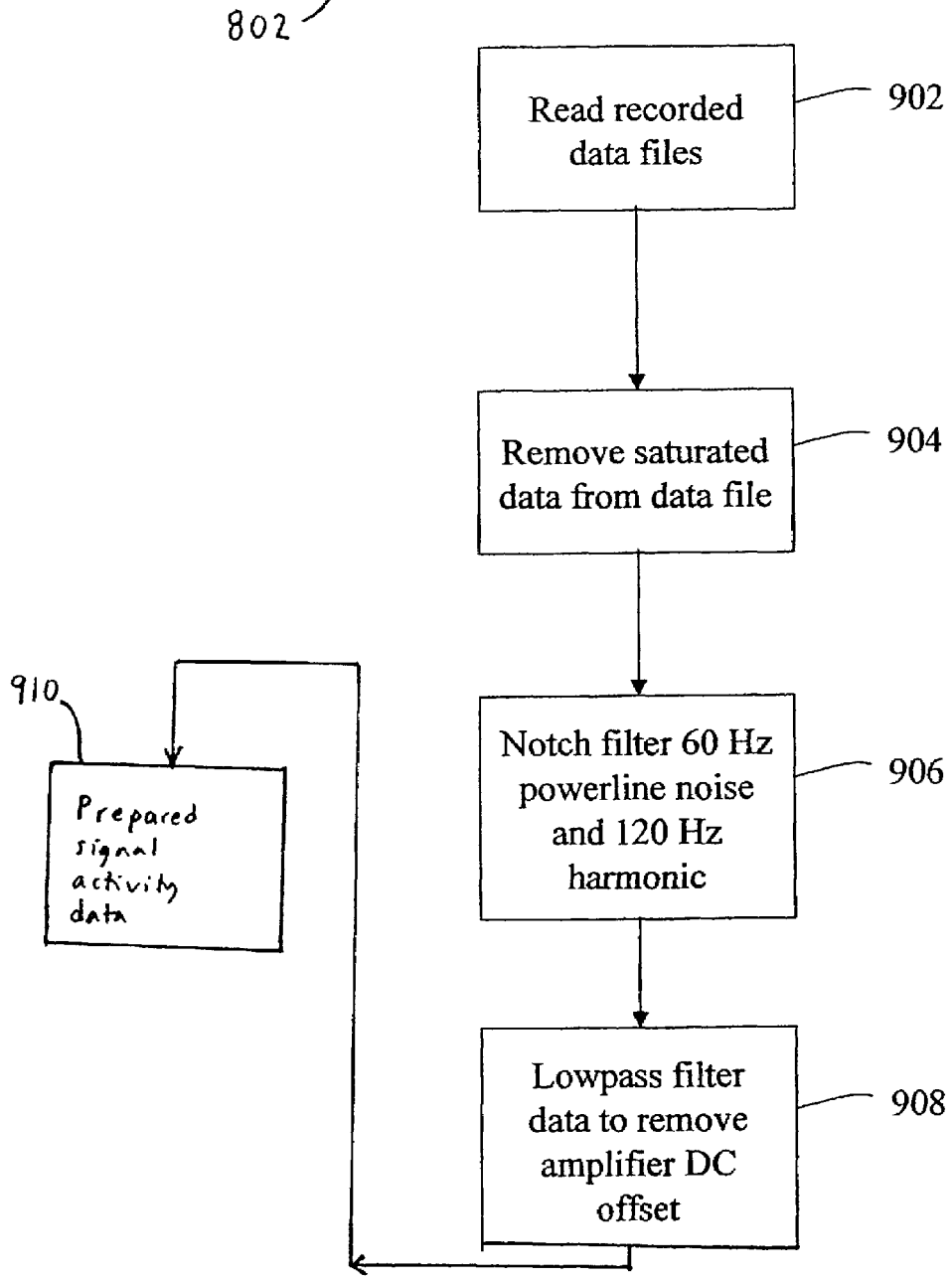
FIG. 9 is a flow diagram illustrating an embodiment of the steps performed for data preparation.
Figure 10:
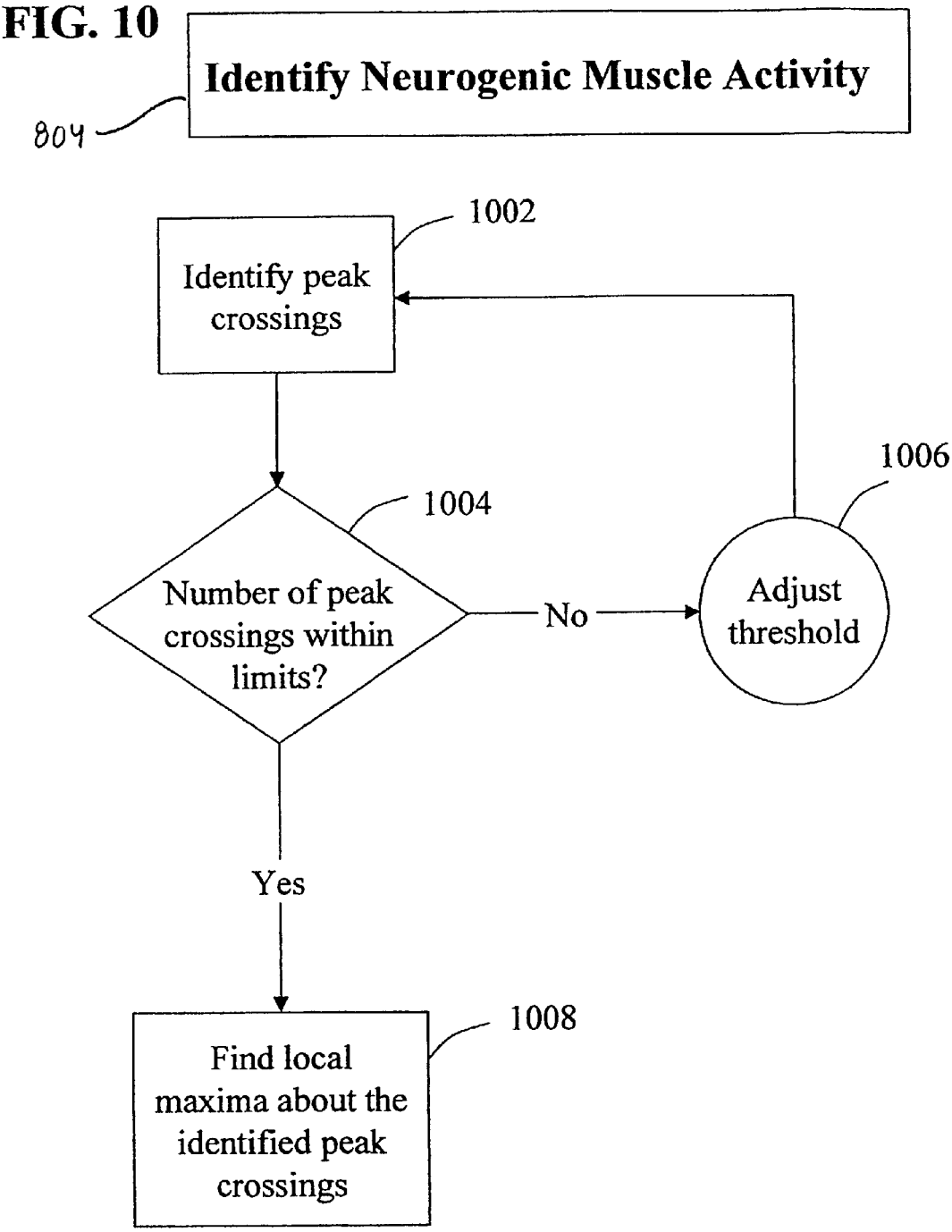
FIG. 10 is a flow diagram illustrating an embodiment of the steps performed to identify neurogenic muscle activity.

FIG. 8 is a flow diagram illustrating an embodiment of the method steps performed by the spontaneous muscle activity signal processing algorithms. A first step 802 prepares the recorded signal activity data. Referring to FIG. 9, step 802 involves a first substep 902 comprising reading a recorded data file, a second substep 904 comprising removal of saturated data from the data file, a third substep 906 comprising filtering noise, and a fourth substep 908 comprising the removal of any DC offset. Referring again to FIG. 8, a next step 804 identifies a neurogenic motor activity from prepared signal activity data 910. Referring now to FIG. 10, step 804 comprises a first substep 1002 of identifying peak crossings from data 910. A second substep 1004 determines whether the number of peak crossing are within predefined limits. If the number of peak crossings is not within the predefined limits, then a substep 1006 adjusts the threshold before repeating substep 1002 and substep 1004. If the number of peak crossings is within the predefined limits, then a substep 1008 finds the local maxima about the identified peak crossings.

Figure 11:
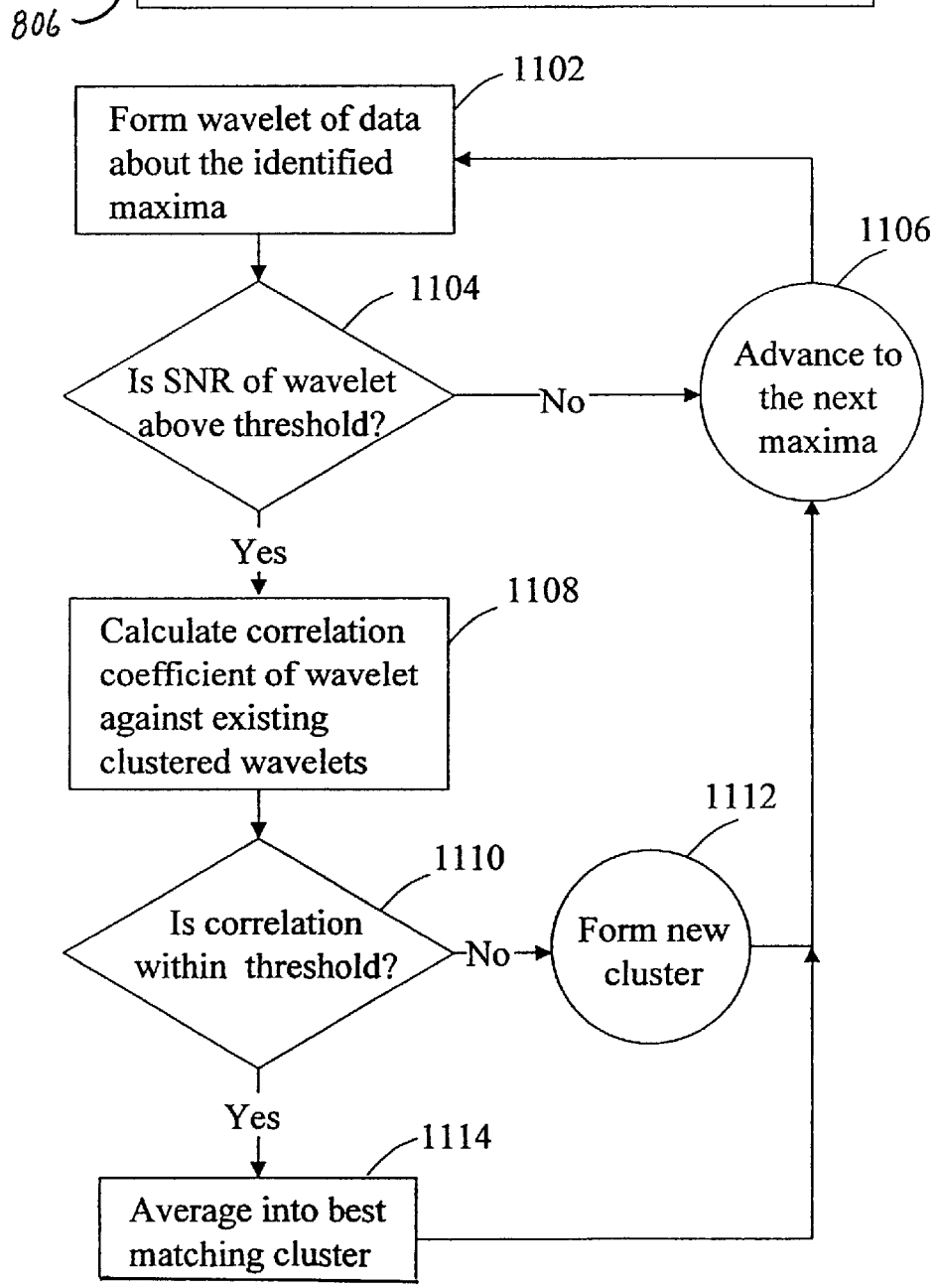
FIG. 11 is a flow diagram illustrating an embodiment of the steps performed for form matched filter templates.

Looking at FIG. 8, a step 806 is provided to form matched filter templates. As seen in FIG. 11, step 806 comprises a substep 1102 of formation of a wavelet about an identified maxima from substep 1008 of step 804. Next, a substep 1104 determines whether the signal to noise ratio (SNR) is not above the given threshold. If the SNR is not above the given threshold, a substep 1106 advances to the next maxima so as to form a wavelet according to substep 1102. If the SNR is above the given threshold, a substep 1108 calculates a correlation coefficient of the wavelet against existing clustered wavelets. A substep 1110 determines if the correlation is within a given threshold. If the correlation is within the given threshold, a substep 1112 forms a new cluster and proceeds to substep 1106 so as to advance to the next maxima. If the correlation is outside of the given threshold, a substep 1114 averages the wavelet into the best matching cluster.

Figure 12:
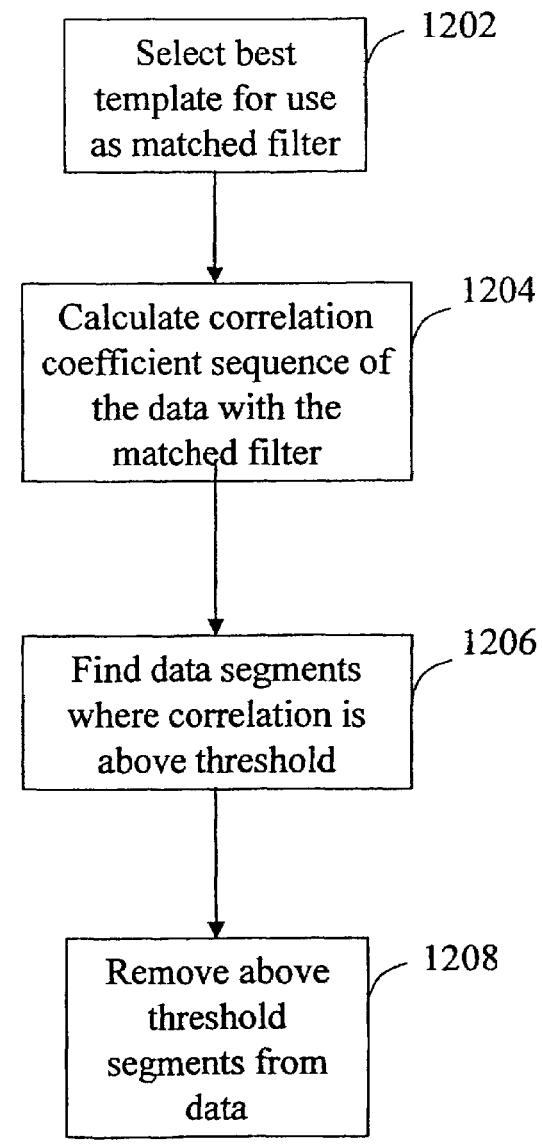
FIG. 12 is a flow diagram illustrating an embodiment of the steps performed to remove neurogenic motor activity.

Referring again to FIG. 8, a step 808 comprises removal of neurogenic motor activity from step 806. Referring now to FIG. 12, step 808 comprises a substep 1202 of selecting a best template for use as a matched filter. A substep 1204 calculates a correlation coefficient sequence of the data with the matched filter. A substep 1206 finds data segments from substep 1204 where correlation is above threshold. A substep 1208 removes above threshold segments of subset 1206 from the data.

Referring now to FIG. 8, neurogenic motor activity is removed from the recorded signal activity by steps 804, 806 and 808. The neurogenic motor activity is removed as if it was noise and non-neurogenic signal activity data remains in the remaining signal activity data.

Referring still to FIG. 8, a final step 810 determines the power level of non-neurogenic muscle activity according to the remaining signal activity data. As seen in FIG. 13, step 810 involves a first substep 1302, which comprises calculation of the power signal density of the involuntary signal data for healthy and symptomatic muscles of interest. A second substep 1304 comprises calculation of the energy within a signal bandwidth. A third substep 1306 comprises the calculation of energy in the noise bandwidth. A fourth substep 1308 comprises the calculation of the signal to noise ratio for healthy and symptomatic muscles.

FIG. 9 is a flow diagram illustrating an embodiment of the steps performed for step 802 comprising data preparation of the recorded myoelectrical signal activity data. First substep 902 reads recorded myoelectrical signal activity data files Second substep 904 removes saturated data from the recorded data files. In third substep 906 notch filter removes 60 Hz powerline noise and its 120 Hz harmonic. Fourth substep 908 applies a lowpass filter to the data to remove the amplifier DC offset from the recorded and filtered signal activity data. The DC offset is the signal amplitude added by the signal detection electronics when detecting a signal with an amplitude of 0.

FIG. 10 is a flow diagram illustrating an embodiment of the step 804 performed to identify neurogenic myoelectrical signal activity. A first substep 1002 identifies peak crossings above a signal strength threshold. A second substep 1003 counts the number of peak crossings and tests if the count of peak crossings is within a pair of peak crossing count limits. If the number of peak crossings is not within the pair of peak crossing limits, substep 1006 adjusts the threshold in a direction to increase the likelihood that the number of peak crossings will be within the pair of peak crossing count limits. In other words, if the count of peak crossings is below the lower peak crossing count limit, then the signal strength threshold is lowered. If the count of peak crossings is above the upper peak crossing count limit, the signal strength threshold is raised. In one embodiment, the signal strength threshold is initiated to equal 2 micro-volts and is adjusted by increments of 0.2 micro-volts.

The pair of peak crossing count limits identify a "middle ground" with respect to a numerical range of the number of peak crossing counts. Peak crossing counts above the upper peak crossing count limit indicate noise. Peak crossing counts below the lower peak crossing count limit indicate lack of a signal. In one embodiment, the lower peak crossing count limit is 100 and the upper peak crossing count limit is 2000 within a time duration of 120 ms myoelectric signal activity recording. A final substep 1008 identifies a local maxima about the identified peak crossings using the signal strength threshold that results in the number of peak crossing counts being within the pair of peak crossing count limits.

The purpose of step 804, which comprises substeps 1002-1008, is to identify nerve initiated motor unit action potentials (MUAPs) for forming a matched filter. These substeps 1002-1008 identify peaks within the time domain of the myoelectric signal activity data that have a high probability of being motor unit action potentials. These identified peaks are used to form the matched filter, which can then be applied to the myoelectric signal activity data so as to find MUAPs that may be not clearly discernible from other signal activity including noise.

In one embodiment, peaks are identified from the myoelectric signal activity data by first maximizing the local peaks by applying the following transform of the myoelectric signal activity data. In one embodiment, this transform is expressed as: $y[n]=x[n]*x[n]-x[n+a]*x[n-a]$, where $x[n]$ is the data sequence at a point 'n' and 'a' is an offset that corresponds to 0.5 ms.

The data sequence represents signal amplitude in the time domain. In other embodiments, variants of this transform can be used with this algorithm. The effect of this transform is to emphasize peaks and their difference from other signal activity including noise.

The output sequence $y[n]$ is susceptible to noise peaks. To remove the effect of noise and differentiate noise peaks from true MUAPs, this algorithm uses a short term average sequence, $sta[n]=sum\ of\ y[n+b]/N$, where b ranges from $-N/2$ to $N/2$. N is determined to average over 5 ms. A long term average, $lta[n]=sum\ of\ y[n+c]/M$, where c ranges from $-M/2$ to $M/2$, is also used with this algorithm. M is determined to average over 20 ms.

Both the short term average (sta) and the long term average (lta) are compared to identify MUAPs. For peaks created by other signal activity such as noise, the difference between the short term average (sta) and the long term average (lta) will be slight, for true MUAPs the short term average (sta) will be much larger than long term average (lta). When the short term average (sta) is greater than twice the long term average (lta), expressed as $sta>2*lta$, that point is identified as being the site of a MUAP. The length of a window (50 ms) is advanced to continue searching for the next MUAP.

For each myoelectric signal activity data point identified as corresponding to a MUAP, a 50 ms window is centered about that point and the maximum in that window is located by taking the first derivative of the data in that window and finding the zero point. The listing of data points are considered to be corresponding to clearly discernible MUAPs, which form the matched filter.

FIG. 11 is a flow diagram illustrating an embodiment of substeps 1102-1114 performed to form matched filter templates. First substep 1102 forms a wavelet of data about the identified maxima. Second substep 1104 determines whether the signal to noise ratio (SNR) of the wavelet is above a threshold 1104. In one embodiment, 10 dB is used as the given SNR threshold. If the signal to noise ratio is not above the threshold, then substep 1106 advances to the next maxima and returns to substep 1102. If the signal to noise ratio is above the given SNR threshold, then the substep 1108 calculates a correlation coefficient of the one or more characteristics of the wavelet against existing one or more characteristics of each clustered wavelet.

Next, substep 1110 tests whether the correlation coefficient is above a threshold. If the correlation coefficient is not above the threshold, then substep 1112 forms a new cluster and the program proceeds to substep 1106, which advances to the next maxima and then returns to substep 1102. If the correlation coefficient is above the threshold, then substep 1114 averages the one or more characteristics of the wavelet into the one or more characteristics of the best matching cluster and advances to the next maxima and returns to substep 1102 to form a wavelet of data about an identified maxima. This method terminates after processing all identified maxima.

The purpose of substeps 1102-1114 is to form a matched filter template, which is used for removing neurogenic muscle activity from the myoelectric activity signal activity data. In one embodiment, to form a matched filter template, for each maxima identified in the previous substep 1102, a 50 ms window of myoelectric activity signal activity data is identified and centered about each maxima. In other embodiments, windows of larger or smaller size, such as 20 ms, can be employed. Characteristics of the window of data, referred to as a wavelet, can be measured at locations in the window of data representing time offsets from the maxima or some other reference point. In some embodiments, the signal strength characteristics of the wavelet are measured at time offsets of 10 ms from the maxima.

Based on the correlation of one or more characteristics of each wavelet with those of a wavelet cluster, each window of data is associated with and placed into the highest correlating wavelet cluster. Placing a wavelet in to an associated wavelet cluster averages the one or more characteristics of the wavelet with those one or more characteristics of the associated wavelet cluster. The larger the wavelet cluster, the less effect one wavelet has on the wavelet cluster average for any particular characteristic of the wavelet cluster. The first wavelet of myoelectric signal activity data automatically forms a new wavelet cluster, identified as the first wavelet cluster. Characteristics of the wavelet can include without limitation wavelet associated signal strength, which is represented as signal strength data points located within a time interval of the time domain and indicates the shape of the wavelet over time, upper and/or lower amplitude, wave length, and short and long term averages associated with the wavelet.

Each succeeding wavelet is compared to existing wavelet clusters by calculating the wavelet to cluster correlation coefficient between one or more characteristics of each wavelet cluster and the same one or more characteristics of the wavelet. If there is a match, i.e., the coefficient is greater than 0.4, then the characteristics of the wavelet are averaged into the characteristics of the most correlating existing wavelet cluster. If there is not a match, a new wavelet cluster is formed. The new wavelet cluster corresponds to either a different type of MUAP or other signal activity such as noise. In other embodiments, the coefficient value can be another chosen variable such as 0.3 or 0.5. The best wavelet cluster to use as matched filter template is selected by calculating a KGI index and determining the number of wavelets in the wavelet cluster. In one embodiment, the matched filter must contain at least 20% of the total number of wavelets and have a KGI>15. The data is discarded as a failed data collection if there is not a filter satisfying this criteria. The data is also discarded as a failed collection if the muscle is asymptomatic. If the muscle is analyzed directly and no motor activity can be elicited during a general exam by a physician, this may be due to a complete nerve block.

In one embodiment, the KGI index is based on an average of the power spectrum over the muscle signal band (150-400 Hz) and over the average power spectrum in the noise frequency band (2500-4000 Hz). Other muscle signal bands, preferably between 100-500 Hz, are used in different embodiments. The KGI index is expressed as KGI=10 log (signal/noise) where log is the log base 10. The KGI index is compared between the symptomatic muscle and reference data, such as an asymptomatic muscle and the difference is calculated to determine if spontaneous activity is present.

FIG. 12 is a flow diagram illustrating an embodiment of substeps 1202-1208 performed to remove neurogenic myoelectrical signal activity. First substep 1202 comprises selecting the best matched filter template for use as a matched filter based upon the selection criteria in substeps 1102-1114 of step 806. Second substep 1204 comprises calculating a filter to data correlation coefficient sequence of the myoelectrical signal activity data with the matched filter. Third substep 1206 finds data segments where the correlation coefficient is above a selected threshold and fourth substep 1208 removes these data segments.

In one embodiment, the match filter template selected as the best match filter template based upon the criteria of substeps 1102-1114 of step 806 (FIG. 11) is applied to the myoelectrical signal activity data to remove neurogenic myoelectrical signal activity. Sections of the myoelectrical signal activity in the time domain in which the correlation coefficient between the myoelectrical signal activity data and the matched filter template are calculated to be greater than 0.4 are identified and removed from the myoelectrical signal activity data. Other sections of myoelectrical signal activity data which are at least 100 ms in length are retained for further analysis, with no MUAPs in this section.

FIG. 13 is a flow diagram illustrating an embodiment of the steps performing spectral analysis of the filtered myoelectrical signal activity data. In this embodiment, spectral analysis includes the determination of the power level of motor activity of the retained data from the myoelectrical signal activity data.

First substep 1302 calculates the power signal density (PSD) of the filtered myoelectrical signal activity data for symptomatic muscles and reference data, such as asymtomatic and healthy muscles of interest. Second substep 1304 calculates energy in the signal bandwidth Third substep 1306 calculates energy in the noise bandwidth. Fourth substep 1308 calculates the signal to noise ratio (SNR) for symptomatic muscles and asypmtomatic healthy muscles of interest. A comparison of power signal density (PSD) without noise between symptomatic muscles and reference data is used to reveal any existing neuromuscular pathology. Reference data can be associated with asymtomatic and healthy muscles.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method of non-invasively detecting neuromuscular pathology in an at-rest individual comprising the steps of:
    (a) placing on the skin surface of said individual substantially adjacent to a target skeletal muscle a detector capable of detecting both neurogenic and spontaneous myoelectrical activity;
    (b) obtaining a first signal output from said detector that comprises bioelectrical signals representing the presence of both neurogenic and spontaneous myoelectrical activity within proximity of said skeletal muscle;
    (c) processing said first signal output to remove any signals representative of neurogenic myoelectrical activity, whereby to produce a second signal output;
    (d) processing said second signal output to identify any signals representative of spontaneous myoelectrical activity in said target muscle; and
    (e) determining from said processed second signal output neuromuscular status of said target muscle.

2. The method of claim 1 wherein said second signal output comprises spontaneous myoelectrical activity within a frequency range of 100 to 500 Hz.

3. The method of claim 1 wherein step (c) comprises removing external electrical interference signals from said recorded signals.

4. The method of claim 1 wherein step (c) also comprises removing at least one signal generated from at least one muscle other than said skeletal muscle from said first signal output.

5. The method of claim 1 wherein said processing step (d) comprises determining a power spectral density of said second signal output.

6. The method of claim 5 wherein said power spectral density is determined over a particular frequency range.

7. The method of claim 6 wherein said range is between 100-500 Hz.

8. The method of claim 6 wherein said range is between 300-500 Hz.

9. The method of claim 1 wherein said step (e) comprises comparing at least one characteristic of the processed second signal output against at least one reference value for each of said at least one characteristic.

10. The method of claim 9 wherein step (d) further comprises deriving said at least one characteristic from a power spectral density measurement of said processed second signal output.

11. The method of claim 9 wherein a difference in said at least one characteristic of the processed second signal output as compared to the at least one reference value is an indicator of neuromuscular pathology.

12. The method of claim 5 further comprising displaying the power spectral density of said second signal output.

13. The method of claim 1 further comprising displaying a relative value quantifying the degree of neuromuscular pathology in response to the step of determining neuromuscular status.

14. The method of claim 1 wherein the neuromuscular disease is selected from the group of diseases consisting of radiculopathies, demyelinating neuropathies, intravertebral disc disease, and carpal tunnel syndrome.

15. The method of claim 1 further comprising comparing said processed second signal output at a first point in time to the processed signal output of the individual at a second point in time to monitor the progression of the neuromuscular pathology.

16. A method of detecting neuromuscular disease in an individual comprising the steps of:
    measuring a bioeletrically-generated first signal output from a detector positioned on the skin surface and substantially adjacent to a target skeletal muscle of an individual at rest;
    removing noise from said first signal output to generate a second signal output consisting substantially of myoelectrical activity;
    processing said second signal output to derive a third signal output free of neurogenic myoelectrical activity; and
    determining the neuromuscular status of said individual in response to said processed signal output.

17. The method of claim 16 wherein said noise comprises electrical signals having a frequency less than 0.1 Hz and a electrical signals having a frequency greater than 10 kHz.

18. The method of claim 16 wherein said third signal output also is subjected to a power spectral analysis, and further wherein a given difference in a power spectral density measurement of said third signal output as compared to a reference value is indicative of neuromuscular disease.

19. The method of claim 18 further comprising displaying a power spectral density measurement of said third signal output.

20. The method of claim 16 further comprising determining and displaying a relative value quantifying the degree of neuromuscular disease.

21. A system for detecting neuromuscular disease in an individual, said system comprising:
  a detector positionable on the skin surface of said individual substantially adjacent to a target skeletal muscle and capable of sensing myoelectric activity via said skin surface and generating a first electrical signal output representative of said myoelectric activity;
  at least one means for recording said first signal output from said detector;
  a filter in communication with said recording means for generating from said first signal output a second signal output consisting substantially of signals representative of spontaneous myoelectrical activity; and
  a processor in communication with said filter, said processor being programmed to (a) cause said first signal output from said skeletal muscle to be filtered so as to consist substantially of spontaneous myoelectrical signals, (b) calculates the power spectral density of the filtered second signal output and (c) determine the neuromuscular status in response to the power spectral density of the filtered second signals output.

22. A system for detecting neuromuscular disease in an individual, said system comprising:
  at least one surface recording electrode placed on the skin surface of the individual for detecting bioelectrical potentials in response to myoelectrical activity of a skeletal muscle and to generate a first electrical signal output representative of said potentials;
  means for processing said first signal output to generate a second signal output consisting substantially of signals representative of spontaneous myoelectrical activity; and
  a processor for processing said second signal output and calculating the power spectral density of said signals representative of said spontaneous myoelectrical activity and for determining the presence of disease in skeletal muscle or the presence of nerve innervating skeletal muscle in the individual in response to said power spectral density of said signals representative of said spontaneous myoelectrical activity.

23. The system of claim 22 further including means for removing from said first signal output noise in a first frequency range below about 0.1 Hz and in a second frequency range above about 10,000 Hz.

24. A method of non-invasively detecting neuromuscular pathology in an at-rest individual comprising the steps of:
  (a) placing a bioelectric signal detector on the skin surface of an at-rest individual substantially adjacent or proximate to a target skeletal muscle of that individual;
  (b) using said detector to detect and capture myoelectric signals from said individual while said individual is at rest;
  (c) filtering said myoelectric signals to eliminate signals having a frequency less than 0.1 Hz and greater than 10 kHz;
  (d) processing said filtered myoelectric signals via a plurality of transformations to improve the signal-to-noise ratio of said signals;
  (e) further processing said myoelectric signals to identify and remove any neurogenic myoelectric signal activity;
  (f) subjecting said myoelectric signals to spectral analysis to determine the power spectral density of said signals; and
  (g) using said power spectral density to determine the presence and extent of neuromuscular pathology of said target muscle.

25. Method according to claim 24 wherein step (f) comprises determining the power spectral density of said myoelectric signals within a frequency band of 100 to 500 Hz.

26. Method according to claim 24 wherein said step (g) comprises comparing the power spectral density of said myoelectric signals to one or more characteristics of myoelectric signals detected at a second point in time.

27. Method according to claim 25 wherein said step (g) comprises comparing the power spectral density of said myoelectric signals to a reference value.

28. Method according to claim 25 wherein said step (c) also comprises amplifying said myoelectric signals by a factor in the order of thousands.

* * * * *